United States Patent
Lyle et al.

[11] Patent Number: 6,114,290
[45] Date of Patent: Sep. 5, 2000

[54] DETERGENT COMPOSITION

[75] Inventors: Ian Gardner Lyle, Buxtehude, Germany; Mavis Claire Pereira; Jason Richard Williams, both of Bebington, United Kingdom

[73] Assignee: Lever Brothers Company, Division of Conopco, Inc., New York, N.Y.

[21] Appl. No.: 09/185,828

[22] Filed: Nov. 4, 1998

[30] Foreign Application Priority Data

Nov. 7, 1997 [GB] United Kingdom ............... 9723643
Nov. 7, 1997 [GB] United Kingdom ............... 9723644

[51] Int. Cl.⁷ ............................. C11D 3/20; A61K 7/00
[52] U.S. Cl. .................... 510/120; 510/130; 510/136; 510/139; 510/158; 510/159; 510/404; 510/406; 510/407; 424/401; 514/844
[58] Field of Search ................... 510/406, 120, 510/136, 139, 130, 158, 159, 404, 407; 424/401; 514/844

[56] References Cited

U.S. PATENT DOCUMENTS

| | | | |
|---|---|---|---|
| 3,691,270 | 9/1972 | Charle et al. ................ | 424/401 |
| 4,335,103 | 6/1982 | Barker et al. ............... | 424/59 |
| 4,348,292 | 9/1982 | Ginn ........................... | 252/90 |
| 5,013,473 | 5/1991 | Norbury et al. ............. | 424/452 |
| 5,165,917 | 11/1992 | Zabotto et al. ............. | 424/70 |
| 5,179,128 | 1/1993 | Lyle et al. . | |
| 5,468,496 | 11/1995 | Touzan et al. .............. | 424/401 |
| 5,612,307 | 3/1997 | Chambers et al. .......... | 510/406 |
| 5,929,019 | 7/1999 | Puwada et al. ............. | 510/406 |

FOREIGN PATENT DOCUMENTS

| | | |
|---|---|---|
| 0468703 | 1/1992 | European Pat. Off. . |
| 0728475 | 12/1995 | European Pat. Off. . |
| 6-51615 | 7/1994 | Japan . |
| 81567865 | 6/1996 | Japan . |
| 1038492 | 8/1966 | United Kingdom . |
| 2246363 | 1/1992 | United Kingdom . |
| 2310813 | 9/1997 | United Kingdom . |
| 95/16023 | 6/1995 | WIPO . |
| 96/02230 | 2/1996 | WIPO . |
| 97/28780 | 8/1997 | WIPO . |

*Primary Examiner*—Lorna M. Douyon
*Attorney, Agent, or Firm*—Alan A. Bornstein

[57] ABSTRACT

An aqueous cleansing and oily soil removing composition comprising a surface active agent and an agent for removing oily soil from skin, in which the surface active agent and agent for removing oily soil are separate but combinedly dispensable from a single packaging means as discrete domains, preferably in a predetermined ratio. Separating the agent for removing oily soil from the surface active agent results in improved removal of oily soil from skin, and a clean, fresh feel which is appreciated by the consumer.

12 Claims, No Drawings

DETERGENT COMPOSITION

The present invention relates to detergent compositions suitable for topical application for cleansing and removing oily soil from the human body, particularly for removing make-up from the skin, lips, hair, and nails. In particular, it relates to such compositions which are formulated to remove make-up effectively while delivering the clean, refreshed skin feel benefits normally associated with foaming cleansers.

Compositions formulated to remove make-up from the skin are well known. These generally contain high levels of solvents, such as cosmetic oils, which are effective in penetrating and dispersing the oily layer of waxes and pigment particles which constitutes the make-up soil. Such make-up remover compositions may be designed for wipe-off, for example, using a cotton pad, or may be designed for rinse-off with water, in which case they may also contain surfactants to allow co-emulsification of the make-up base and solvent oil.

However, it is normally found that make-up removers which are thus formulated as oils or emulsions of water/oil or oil/water type leave the skin with a greasy after-feel. They also tend to be non-foaming or to provide very little lather during rinse-off. Consumer preference in the main is for a clean, refreshed skin feel after cleansing. The desire to achieve this result, especially when heavy make-up has been worn, frequently results in following a double cleansing routine.

Conventional foaming cleansers, such as bar soaps, facial washes, bath foams, shampoos and shower gels, are well known which provide copious lather on mixing with water, remove light soil (for example sebum) from the skin surface and leave the skin feeling clean and refreshed. However, such products tend to be rather poorly effective at removing heavy soil like make-up.

In recent years, a new class of "2-in-1" cleansers has emerged, which are claimed to combine the benefits of effective make-up removal with the easy rinsability, lathering and skin feel attributes normally associated with foaming cleansers. The failure of these products to win significant market share is a consequence of the compromises that have had to be made in their formulation. Thus, known "2-in-1" cleansers which have been derived from conventional facial foam formulations fail to remove make-up completely, while those which have been derived from conventional make-up remover formulations fail to deliver the sensory benefits associated with thoroughly clean, refreshed skin.

It is also known to formulate another class of "2-in-1" products which provide both a cleansing and a moisturising benefit. For example WO 96/02230 discloses a composition comprising a surface active agent and a benefit agent in which the surface active agent and benefit agent are separate but combinedly dispensable from a single packaging means in a predetermined ratio as discrete domains. Separating the benefit agent from the surface active agent is said to result in improved deposition of the benefit agent. However, whereas WO 96/02230 is concerned with depositing a substance onto the skin, the present invention achieves the reverse effect of removing a substance from the skin.

One of the problems which may typically be encountered with such dual purpose compositions is that they contain an insufficient level of remover component or an insufficient amount is effectively active in use.

Another problem associated with such dual cleansing and moisturising or soil-removing compositions is instability. According to WO 94/03152, concerned with shower gels comprising a non-soap detergent, silicone oil and cationic polymers, the maximum average droplet size of the silicone oil that can be used is 2 microns, if product stability is to be maintained.

We have found a way of formulating such compositions such that they can deliver effective oily soil removal, while still providing the sensory benefits associated with foaming cleansers.

Further, we have found that the stability of a dual cleansing and soil removing product, and delivery and effectiveness of the removal agent can be improved by providing a composition in which the cleansing and removal components are separate but combinedly dispensable from a packaging means as discrete domains.

Thus, according to a first aspect of the invention, there is provided a cleansing and oily soil removing liquid composition comprising:

a) an aqueous domain containing one or more surface active agents selected from anionic, nonionic, amphoteric, zwitterionic and cationic surfactants, soaps and mixtures thereof; and b) an aqueous or non-aqueous domain containing one or more agents for removing oily soil, said aqueous or non-aqueous domain being in a non-emulsified state;

wherein the domains are greater than 1000 microns in size, and are separate but combinedly dispensable from a single packaging means as discrete domains.

The composition is suitable for thoroughly cleansing the skin. The removal agent is included in the composition to remove oily soil, such as make-up from the skin.

The invention also provides a method for improved removal of oily soil from the skin by using the aforementioned cleansing and oily soil removing composition, the method comprising:

i) dispensing the surface active agent and the agent for removing oily soil from a packaging means;

ii) applying the surface active agent and the agent for removing oily soil to the human body; and iii) removing the resulting mixture of oily soil and cleansing agents by rinsing with water.

In a further embodiment, the invention also provides a packaged cleansing composition for topical application and use. A suitable package for use in this embodiment of the invention is preferably a multiple compartment package, such as a two compartment package.

An advantage of the present invention is that it leads to improved removal of oily soil by a surface active agent containing aqueous liquid composition during use. The surface active agent and removal agent are separated in the composition, and may even not directly contact one another in the composition. The latter situation allows avoidance of adverse interactions which may occur between the two components that may result in ineffective action of the removal agent.

Without being bound by theory, it is believed that the removal agent is dispersed into relatively large droplets during rubbing-in of the composition in use, and these droplets readily remove oily soil, such as make-up, from the skin. By separating the domains of removal agent and aqueous foaming surfactant, in the case where the former contains water-immiscible components, it is unnecessary to employ emulsion technology to prepare the initial composition. It is believed that the relatively large droplets, formed in situ during rubbing in of the composition and facilitated by the dispersing of the oily soil removal phase as a single phase or domain, are more effective than relatively small emulsion droplets in removing oily soil. Make-up removal may be enhanced by delivering the effective agents to the make-up film in locally high concentration. The relatively large droplets are then though to be reduced in size during use, due to the rubbing action used during application, thus facilitating their dissolution as a dispersed phase in the aqueous surfactant phase of the composition.

The invention offers additional advantages not necessarily related to efficacy, as such, but more related to the problems of avoiding formulation instability and delivering other consumer benefits, which include:

(a) incompatibility of formulation ingredients, which might lead to instability and separation during storage, can be avoided by partitioning the ingredients into different domains; when, for example, high levels of polyethylene glycols are preferred constituents of the removal agent, phase separation of aqueous surfactant can be avoided by formulating all or most of the polyethylene glycol into the other, oily soil removing, domain.

(b) two structuring systems may be used to provide optimal product viscosity, consumer feel and appearance, for each domain, with the structuring systems being more closely adapted to the requirements of each domain;

(c) two preservative systems may be used for optimal stability for each domain, with the preservative systems being more closely adapted to the requirements of each domain;

(d) similarly, two dye/pigment systems for each domain may be used to convey a consumer benefit, for example to reinforce the concept that the product is an effective and true 2-in-1 product;

(e) formulation ingredients may be kept in separate domains until use when they may react to give a consumer-perceivable sensation, for example heat generation, change in viscosity or appearance;

(f) any UV-light sensitive material may be kept in only one chamber with UV filtering ability, thus allowing a cost saving on quantity of such UV filtering packaging; and (g) use of multiple chamber packaging rather than a single chamber may reduce path length of light through the product, thus improving apparent clarity.

The surface active agent to be contained in the aqueous domain of the composition may be selected from any known surfactants suitable for topical application to the human body. Mild surfactants, i.e. surfactants which do not damage the stratum corneum, the outer layer of skin, are particularly preferred.

One preferred anionic detergent is fatty acyl isethionate of formula:

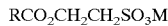

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend. Another preferred anionic detergent is alkyl ether sulphate of formula:

where R is an alkyl group of 8 to 22 carbon atoms, n ranges from 0.5 to 10 especially from 1.5 to 8, and M is a solubilising cation as before.

Other possible anionic detergents include alkyl glyceryl ether sulphates, sulphosuccinates, taurates, sarcosinates, sulphoacetates, phosphates, phosphate esters and ethoxylated phoshates; and acyl lactylates, glycinates, alaninates and glutamates; and mixtures thereof.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein $R^5$ ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Amino acid surfactants include acyl alaninates, acyl glycinates and acyl glutamates identified by the formulae:

Alaninates:

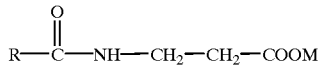

where R is an alkyl or alkenyl group of 7 to 21 carbon atoms and M is a solubilising cation such as sodium, potassium, ammonium or substituted ammonium. Acyl alaninates may be derived from L-alanine:

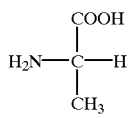

or from β-alanine:

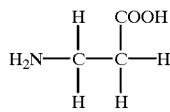

Glycinates:

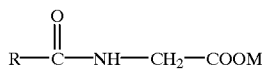

where R is an alkyl or alkenyl group of 7 to 21 carbon atoms and M is a solubilising cation such as sodium, potassium, ammonium or substituted ammonium.

Glutamates:

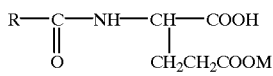

where R is an alkyl or alkenyl group of 7 to 21 carbon atoms and M is a solubilising cation such as sodium, potassium, ammonium or substituted ammonium.

Harsh surfactants such as primary alkane sulphonate or alkyl benzene sulphonate will generally be avoided.

If the surface active agent comprises soap, the soap is preferably derived from materials with a $C_8$ to $C_{22}$ substantially saturated carbon chain and, preferably, is a potassium or triethanolamine soap with a $C_{12}$ to $C_{18}$ carbon chain.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

Suitable amphoteric surface active agents include derivatives of alkyl hydroxyethyl imidazolines such as alkylamphoacetates, alkylamphopropionates, alkylamphodiacetates and alkylamphodipropionates identified by the formulae:

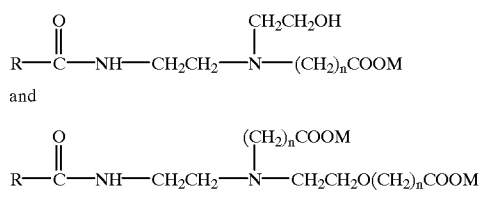

where R is an alkyl or alkenyl group of 8 to 20 carbon atoms, n is 1 or 2, and M is a solubilising cation such as sodium, potassium, ammonium or substituted ammonium.

Mixtures of any of the foregoing surface active agents may also be used.

The surface active agent is preferably present in the overall composition at a level of from 5 to 40 wt %, more preferably 10 to 25 wt %.

It is also preferable that the composition includes from 1 to 10 wt % of a cosurfactant agent with foam boosting or skin-mildness benefits. Suitable materials are zwitterionic detergents which have an alkyl or alkenyl group of 7 to 18 carbon atoms and comply with an overall structural formula:

$$R^1\text{—}[C(=O)\text{—}NH(CH_2)_{\overline{m}}]_n\text{—}\underset{\underset{R^3}{|}}{\overset{\overset{R^2}{|}}{N^+}}\text{—}X\text{—}Y$$

where $R^1$ is alkyl or alkenyl of 7 to 18 carbon atoms $R^2$ and $R^3$ are each independently alkyl, hydroxyalkyl or carboxyalkyl of 1 to 3 carbon atoms;

m is 2 to 4;

n is 0 or 1;

X is alkylene of 1 to 3 carbon atoms optionally substituted with hydroxyl; and

Y is $-CO_2^-$ or $-SO_3^-$.

Zwitterionic detergents within the above general formula include simple betaines of formula:

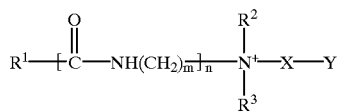

and amido betaines of formula:

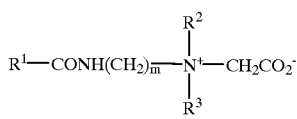

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the group $R^1$ has 10 to 14 carbon atoms. $R^2$ and $R^3$ are preferably methyl.

A further possibility is a sulphobetaine of formula:

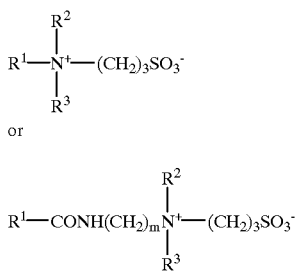

where m is 2 or 3, or variants of these in which $-(CH_2)_3SO_3^-$ is replaced by

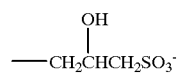

$R^1$, $R^2$ and $R^3$ in these formulae are as defined previously.

The removal agents used in compositions according to the invention may comprise straight or branched chain hydrocarbons (for example mineral oil, isohexadecane), esters (for example isopropyl palmitate), silicones (for example cyclomethicone), natural or synthetic triglycerides (for example castor oil, sunflower oil, macadamia nut oil, glyceryl tri(2-ethylhexanoate)) and plant extracts (for example Witch hazel, Cornflower extract).

However, preferably the removal agent may comprise:
a) polymeric polyols such as polyethylene glycols (for example PEG 200–600);
b) polyhydric alcohols such as propylene glycol, glycerol and sorbitol;
c) solid particulate materials of size greater than 10 microns such as micronised polyethylene or silica;
d) solvents such as ethanol;
e) nonionic surface active agents having HLB numbers<10; and
f) mixtures thereof.

Particularly preferred removal agents include PEG-400 and glycerol.

The domain comprising the removal agent may also contain water, in an amount from 0 to 70%. It may also contain one or more hydrophilic surface active agents which are included to facilitate formation of an oil-in-water emulsion during the final rinsing step, provided that such an emulsion is not present in the formulated domain.

The removal agent is preferably present in the overall composition in an amount of from 1 to 70 wt %, most preferably from 5 to 50 wt %.

Other possible optional ingredients include structurants or thickeners, which may be added to either or both phases of the composition to maintain stability during storage and provide appropriate viscosity during dispensing and use.

Suitable materials for structuring the aqueous foaming surfactant phase include electrolytes which may induce changes in size or geometry of surfactant micelles; water soluble polymers which are tolerant to surfactants; and inorganic materials such as clays or amorphous silica.

The choice of preferred thickeners for the second phase comprising the removal agent depends on whether this phase is aqueous or non-aqueous (for example, whether it is oil or polyol based). Suitable thickeners for aqueous or polyol-based phases include hydrophilic polymers; inorganic materials and mixtures thereof. Suitable thickeners for oil-based phases include oil soluble polymers, waxes, and inorganic materials, particularly those which are hydrophobically modified.

Further examples of structurants and thickeners are given in the International Cosmetic Ingredient Dictionary, Fifth Edition, 1993, published by CTFA (The Cosmetic, Toiletry & Fragrance Association), incorporated herein by reference.

Other typical components of such compositions may preferably include opacifiers, preferably 0.05 to 0.5 wt %; preservatives, preferably 0.05 to 1.0 wt %; and perfumes, preferably 0.1 to 0.5 wt %.

In relation to the physical presentation of compositions according to the invention, it is an essential feature of the invention that the oily soil removing solution and aqueous foaming surfactant solution are separate but combinedly dispensable from a packaging means. Typically, the latter may be a single packaging means. Such a packaging means includes those systems which comprise two or more separate compartments. A wide variety of such packaging means are known in the art, including dual compartment pump dispensers and double tubes which may be configured with the compartments side-by-side or with one inside the other. Particular examples include the multi-cavity dispensing container described in U.S. Pat. No. 5,020,694 and the multi-chamber tube described in U.S. Pat. No. 4,964,539.

Preferably the aqueous surface active agent and the removal agent may be dispensable from a single packaging means, for example in a predetermined ratio according to the use for which the composition is intended. An advantage of dispensing the surface active agent and removal agent in combination is that it avoids the inconvenience of having to post-mix the two components. This is particularly advantageous when the separate components of a composition need to be mixed in precise ratios in order to achieve the desired effect.

Although in the preferred situation, the single packaging means may comprise dual-compartments, wherein the aqueous surface active agent and oily soil removal agent are separately contained, a greater number of compartments is possible, and even a unitary compartment system can be envisaged.

For example, in a unitary system, the discrete domains of the composition of the invention may be realised as separate stripes of surface active agents and of removal agent, or as droplets of one agent suspended in the other, optionally in encapsulated form.

Another method of ensuring that the surface active agent and removal agent are separate involves filling of the separate domains of the composition into a single chamber pack by coextrusion or injection, such that suspended droplets or a striped product is produced in which individual stripes or droplets contain either the surface active agent or removal agent.

Compositions of the invention may be formulated as products for washing the skin, for example, facial or hand washing compositions; bath or shower gels; or products for washing the hair.

The compositions of the invention generally may be pourable liquids or semi-liquids e.g. gels or pastes The invention will be further illustrated by reference to the following non-limiting examples.

EXAMPLE 1

The following two formulations were prepared, constituting the two domains of the cleansing composition:

(a) Aqueous surfactant solution (Raw materials 100% active unless otherwise specified)

| Chemical name | Trade name/Supplier | Wt % |
| --- | --- | --- |
| KMAP/DAP + minors | Priori B300D (29% a.i + 9% minors)/Kao | 99.95 |
| Dye/Pigment | Patent Blau V80/Hoechst | 0.0001 |
| 5-Chloro-2-methyl-4-isothiazolin-3-one and 2-methyl-4-isothiazolin-3-one (1.5% aq.sol.) | Kathon CG/Rohm and Haas | 0.05 |

Manufacture: To Priori B-300D the preservative was first added and mixed. The dye/pigment was then added and mixed.

(b) Oily soil remover

| Chemical name | Trade name/Supplier | Wt % |
| --- | --- | --- |
| Mono-isopropanolamine laureth sulphate (2 Eo) | Zetesol 856/Zschimmer & Schwarz | 16.00 |
| Laureth-4 | Brij 30/Sigma | 6.00 |
| Coco monoethanolamide | Empilan CME/Albright and Wilson | 5.50 |
| Precipitated silica | Sorbosil TC15/Crosfield | 12.00 |
| Perfume | Phoenix 3000 OPTFW/Givaudan | 0.10 |
| 5-Chloro-2-methyl-4-isothiazolin-3-one and 2-methyl-4-isothiazolin-3-one (1.5% aq.sol.) | Kathon CG/Rohm and Haas | 0.05 |
| Titanium dioxide | Tiona AG/SCM | 2.00 |
| Macadamia Nut Oil | Macadamia Nut Oil/Jan Dekker | 58.35 |

Manufacture: Macadamia nut oil, Brij 30 and Zetesol 856 were first mixed and heated to 80 degrees C. Sorbosil TC15 was added and mixed under vacuum. Pre-melted Empilan CME was added over the top and mixed in. Titanium dioxide was then added and mixed. After cooling to room temperature the perfume and preservative were added and mixed in.

The package used in this example was a dual compartment pump dispenser of the type described in U.S. Pat. No. 5,020,694, incorporated herein by reference. Such a dispenser comprises two hollow and separate parallel cylinders, these having one end generally closed and the other end telescopically and slidingly accommodating two parallel pistons which conform to ride sealingly along the interior walls of said cylinders so as to force the liquid products contained therein to flow towards said first ends of the cylinders upon relative compression of the cylinders and pistons. The cylinders are provided with outlet channels communicating with an outlet means having adjacent outlet openings and means for causing the liquid products to flow towards each other at the outlet openings to form a single, banded, unmixed stream of the products. The aqueous surfactant solution and oily soil removing solution were filled into the parallel chambers of the dispenser such that the total composition in the dispenser comprised, by volume, 50% remover solution and 50% aqueous surfactant solution.

EXAMPLE 2

(a) Aqueous surfactant solution (raw materials approx. 100% active unless otherwise specified)

| Chemical Name | Trade Name/Supplier | Wt % |
| --- | --- | --- |
| Lauryl MAP/DAP (78/22) | Phosten HLP/Nikkol | 26.70 |
| Triethanolamine | A-900/Shell | 13.30 |
| Perfume | Pheonix 3000 OPTFW/Givaudan Roure | 0.20 |
| 5-Chloro-2-methyl-4-isothiazolin-3-one and 2-methyl-4-isothiazolin-3-one (1.5% aq.sol.) | Kathon CG/Rohm & Haas | 0.05 |
| Water | | 59.75 |

Manufacture: The water and lauryl phosphoric acid were mixed together and heated to 80° C. The acid was neutralised to pH 7.0 with triethanolamine. After cooling to room temperature, the perfume and preservative were added with mixing.

(b) Oily soil remover

| Chemical Name | Trade Name/Supplier | Wt % |
| --- | --- | --- |
| Polyethylene glycol 400 | PEG 400/Sanyo Kasei | 90.00 |
| 5-Chloro-2-methyl-4-isothiazolin-3-one and 2-methyl-4-isothiazolin-3-one (1.5% aq.sol.) | Kathon CG/Rohm & Haas | 0.05 |
| Water | | 9.95 |

Manufacture: Water and PEG 400 were mixed together. The preservative was then added and mixed in.

Formulation domains (a) and (b) were filled separately into the chambers of a dual compartment pump dispenser of the type described in Example 1 above, so that the final composition comprised equal volumes of the aqueous surfactant and oily soil remover domains.

When domains (a) and (b) were combined in equal parts, the total formulation was hazy and quickly phase separated due to flocculation and loss of viscosity. However, when the formulation ingredients were kept in their separate domains within the dual chamber pack, the stability problem was avoided and the materials in both chambers remained transparent.

EXAMPLE 3

(a) Aqueous surfactant solution (raw materials approx 100% active unless otherwise specified)

| Chemical Name | Trade Name/Supplier | Wt % |
| --- | --- | --- |
| K Lauryl MAP/DAP + minors | Priori B300D (29% a.i. + 9% minors) /Kao | 88.85 |
| Precipitated Silica | Sorbosil TC15/Crosfield | 11.00 |
| Perfume | Pheonix 3000 OPTFW/Givaudan Roure | 0.10 |
| 5-Chloro-2-methyl-4-isothiazolin-3-one and 2-methyl-4-isothiazolin-3-one (1.5% aq.sol.) | Kathon CG/Rohm & Haas | 0.05 |

Manufacture: Sorbosil TC15 was added to the Priori B-300D and mixed under vacuum. Perfume and preservative were then added and mixed in.

(b) Oily soil remover

| Chemical Name | Trade Name/Supplier | Wt % |
| --- | --- | --- |
| Polyethylene glycol 400 | PEG 400/Sanyo Kasei | 30.00 |
| Glycerol | Maruko RG/NOF | 30.00 |
| Carbomer | Carbopol ETD2020/Goodrich | 1.33 |
| Triethanolamine | A-900/Shell | 0.38 |
| 5-Chloro-2-methyl-4-isothiazolin-3-one and 2-methyl-4-isothiazolin-3-one (1.5% aq.sol.) | Kathon CG/Rohm & Haas | 0.05 |
| Water | | 38.24 |

Manufacture: The Carbopol ETD2020 was dispersed in the water under high shear mixing. The PEG 400, glycerol and preservative were then added and mixed in. The solution was then neutralised to pH 7.0 with the triethanolamine, with continuous stirring under vacuum.

Formulation domains (a) and (b) were filled separately into the chambers of a dual compartment pump dispenser of the type described in Example 1 above, so that the final composition comprised equal volumes of the aqueous surfactant and oily soil remover domains.

When domains (a) and (b) were combined in equal parts, the total formulation was hazy and quickly phase separated due to flocculation and loss of viscosity. However, when the formulation ingredients were kept in their separate domains within the dual chamber pack, the stability problem was avoided and the material in chamber (b) remained transparent while that in chamber (a) was opaque.

The products dispensed using the formulations in Examples 1, 2 and 3 were tested against known "2-in-1" cleansers presently on the market, according to the method of the invention. The inventive compositions provided substantially increased make-up removal from the skin as well as delivering a consumer appreciated clean and fresh feel.

EXAMPLE 4

(a) Aqueous surfactant solution (raw materials approx. 100% active unless otherwise specified)

| Chemical name | Trade name/Supplier | Wt % |
| --- | --- | --- |
| K MAP/DAP + minors | Priori B300D (29% a.i. + 9% minors)/Kao | 55.75 |
| Polyethylene Glycol 400 | Peg 400/Fisher | 16.00 |
| Precipitated Silica | Neosil CT15/Crosfield | 12.00 |
| Glycerol | Maruko RG/NOF | 16.00 |
| Perfume | Pheonix 3000 OPTFW/Givaudan Roure | 0.20 |

-continued

| Chemical name | Trade name/Supplier | Wt % |
|---|---|---|
| 5-Chloro-2-methyl-4-isothiazolin-3-one and 2-methyl-4-isothiazolin-3-one (1.5% aq.sol.) | Kathon CG/Rohm and Haas | 0.05 |

Manufacture: The Priori B-300D, PEG 400 and glycerol were mixed together. Neosil CT15 was then added and mixed in under vacuum. Finally, the perfume and preservative were added and mixed in.

(b) Oily soil remover

| Chemical Name | Trade Name/Supplier | Wt % |
|---|---|---|
| Carboxyvinylpolymer | Carbopol Ultrez 10/Goodrich | 0.50 |
| Polyethylene glycol 400 | PEG 409/Sanyo Kasei | 16.00 |
| Glycerol | Maruko RG/NOF | 16.00 |
| 5-Chloro-2-methyl-4-isothiazolin-3-one and 2-methyl-4-isothiazolin-3-one (1.5% aq.sol.) | Kathon CG/Rohm & Haas | 0.05 |
| Triethanolamine (90%) | A-900/Shell | 0.55 |
| Water | Distilled Water | 66.90 |

Manufacture: The Carbopol was first dispersed in the water under high shear mixing. The glycerol, PEG 400 and preservative were added with stirring to form a homogeneous dispersion. Mixing was continued under vacuum as triethanolamine was added to neutralise the solution to pH 7.0.

Formulation domains (a) and (b) were filled separately into the chambers of a dual compartment pump dispenser of the type described in Example 1 above, so that the final composition comprised equal volumes of the aqueous surfactant and oily soil remover domains.

The products dispensed using the formulation in Example 4 was additionally tested against known "2-in-1" cleansers presently on the market, according to the method of the invention. The composition of the invention provided substantially increased make-up removal from the skin as well as delivering a consumer appreciated clean and fresh feel.

What is claimed is:

1. A cleansing and oily soil removing composition consisting essentially of:
    a) an aqueous domain, free of an oily soil removal agent, containing one or more surface active agent(s) selected from the group consisting of anionic, nonionic, amphoteric, and zwitterionic surface active agents, soap and mixtures thereof; and
    b) an aqueous or non-aqueous domain, free of a cleansing surface active agent, containing one or more agent(s) for removing oily soil, the nonaqueous domain being in a non-emulsified state; said agents being selected from the group consisting of polymeric polyols, solid particulate materials of size greater than 10 microns, polyhydric alcohols, ethanol, and mixtures thereof;
    wherein the domains are greater than 1000 microns in size and are separate but combinedly dispensable from a single packaging means as discrete domains.

2. A composition according to claim 1, wherein the single packaging means comprises two separate compartments.

3. A composition according to claim 1, wherein one of the domains is in microencapsulated form.

4. A composition according to claim 1, wherein the agent for removing oily soil is thickened with a thickening agent.

5. A composition according to claim 1 wherein the agent for removing oily soil is present in an amount from 1 to 70 wt %.

6. A composition according to claim 1 wherein the agent for removing oily soil is present in an amount from 5 to 50 wt %.

7. A composition according to claim 1, wherein the oily soil is cosmetic make-up.

8. A composition according to claim 1, wherein the aqueous domain containing surface active agent is thickened with a thickening agent.

9. A method for improved removal of oily soil from skin by using a cleasing and oily soil removing liquid composition of claim 1, the method comprising:
    i) dispensing the surface active agent and the agent for removing oily soil from a packaging means;
    ii) applying the surface active agent and the agent for removing oily soil to the human body; and
    iii) removing the resulting mixture of oily soil and cleansing agents by rinsing with water.

10. A method according to claim 9, wherein the surface active agent and the agent for removing oily soil are dispensed from the packaging means.

11. A packaged topical composition comprising a cleansing composition according to claim 1 in a dispensing package.

12. A packaged composition according to claim 11, wherein the package has two or more compartments.

* * * * *